United States Patent [19]

Broad et al.

[11] Patent Number: 5,705,190
[45] Date of Patent: Jan. 6, 1998

[54] CONTROLLED RELEASE FORMULATION FOR POORLY SOLUBLE BASIC DRUGS

[75] Inventors: Neville W. Broad, Sheerness; Alan F. Carmody, Sittingbourne; Liam C. Feely, Aylesford; Brian C. Withers, Maidstone, all of England

[73] Assignee: Abbott Laboratories, Abbott Park, Ill.

[21] Appl. No.: 574,877

[22] Filed: Dec. 19, 1995

[51] Int. Cl.$^6$ ........................................... A61K 9/20
[52] U.S. Cl. ........................ 424/465; 424/484; 424/468
[58] Field of Search .................... 424/78.08, 484, 424/486, 464, 465, 468

[56] References Cited

U.S. PATENT DOCUMENTS

| | | | |
|---|---|---|---|
| 4,172,120 | 10/1979 | Todd et al. | 424/44 |
| 4,289,751 | 9/1981 | Windheuser | 424/181 |
| 4,296,140 | 10/1981 | Jaquith et al. | 426/575 |
| 4,842,866 | 6/1989 | Horder et al. | 424/468 |
| 5,498,424 | 3/1996 | Klein | 424/464 |

FOREIGN PATENT DOCUMENTS

| | | |
|---|---|---|
| 0188 040 | 7/1986 | European Pat. Off. . |
| 60-163 823 | 8/1985 | Japan . |
| 60-163823 | 8/1985 | Japan ............ A61K 31/70 |

*Primary Examiner*—Thurman K. Page
*Assistant Examiner*—P. Kulkosky
*Attorney, Agent, or Firm*—Mona Anand; Thomas D. Brainard

[57] ABSTRACT

A controlled release, oral, solid, pharmaceutical composition for a reduced daily dosage regimen is described where the therapeutic ingredient is a poorly soluble basic drug. The formulation comprises the use of a water-soluble alginate salt, a complex salt of alginic acid and an organic carboxylic acid in admixture with the therapeutic drug. A particular embodiment comprising a once a day dosage form for clarithromycin is also described.

17 Claims, No Drawings

CONTROLLED RELEASE FORMULATION FOR POORLY SOLUBLE BASIC DRUGS

FIELD OF THE INVENTION

This invention relates to a controlled slow release oral dosage form for at least one sparingly soluble basic drug useful to reduce the daily dosage regimen. More particularly, the invention relates to a once daily formulation of clarithromycin.

BACKGROUND OF THE INVENTION

The advent of controlled release dosage forms has provided a benefit to the pharmaceutical industry. Controlled release formulations have allowed the possibility of reducing dosage regimens for drugs, especially those administered orally to outpatients.

The advantages of reduced dosage regimens for the outpatient are convenience and, more importantly, better assurance of compliance. For example, the reduction of a dose regimen from four times a day (q.i.d.) to three times a day (t.i.d.) allows the patient to take the prescribed drug during waking hours. A reduction of a dose regimen to twice a day (b.i.d.) allows the patient to take the prescribed drug in the morning and in the evening, which provides greater convenience; e.g., the patient is not required to carry an additional when away from the home. Of course, the most convenient dosage form is a once daily dose regimen. Unfortunately, the pharmacokinetic properties (e.g., absorption, elimination, and metabolism) of most drugs does not permit them facilely to be prepared in a single oral dosage form and provide controlled efficient release of the drug throughout a 24-hour period with reproducible bioavailability.

One method of improving controlled slow release solid preparations has been the development of preparations containing an alginate gel. Typically, a water soluble alginate such as sodium alginate and calcium ions in the form of a calcium salt are reacted to cross-link the alginate converting it into an insoluble calcium alginate gel. On the addition of a strong acid to the mixture of sodium alginate and calcium salt, the calcium salt is slowly ionized to yield calcium ions. The calcium ions then react with the soluble alginate to form an insoluble calcium alginate gel. Gelation proceeds through gradual ionization of the calcium salt. With these formulations, the controlled release properties of the alginate gel have been varied by varying the molecular weight of alginate, the alginate concentration, the type of polyvalent cation cross-linking agent or the concentration of the cation.

Granted European Patent 188040-B1 and its counterpart, U.S. Pat. No. 4,842,866, describe an improved gel-type alginate composition that is slowly soluble in bodily fluids, such as of the gastrointestinal ("GI") tract, containing a therapeutically effective amount of at least one therapeutically active agent that is gradually released as the alginate hydrates, characterized in that there are present in the preparation both a water-soluble alginate, especially sodium alginate, and a complex salt of alginic acid, especially sodium-calcium alginate, having one cation that alone yields a soluble alginate salt and another cation that alone yields an insoluble alginate salt. The disclosure of the U.S. counterpart, U.S. Pat. No. 4,842,866, is incorporated by reference in its entirety.

The use of the technology developed in the above-mentioned patents, however, was not found to be applicable with poorly water soluble drugs. For example, an in vitro drug release study from an alginate formulation of clarithromycin was observed to be too slow. Similarly, with erythromycin, in vivo animal studies showed that reproducibly bioavailable controlled release formulations were not possible using alginates or any other monolithic hydrogel tablets. It was concluded that macrolides such as erythromycin in a simple monolithic hydrogel tablet will not produce a suitable controlled release dosage form due to the problems of acid instability, poor drug solubility and variable GI transit.

An oral formulation containing 6-O-methylerythromycin A and citric acid with improved bioavailability has been reported in Japanese Kokai 163823/1985, as abstracted in WPI Acc. No. 85-247033/40.

It is an object of the present invention to reduce the daily dose regimen of a poorly water soluble basic drug with a controlled release formulation.

The present invention overcomes the problems of slow release and potentially poor or variable absorption with poorly soluble basic drugs by combining an organic acid and the drug into the alginate formulation.

SUMMARY OF THE INVENTION

The present invention provides for reduced daily dosing of poorly soluble basic drugs by applying the alginate matrix with the incorporation of an organic acid. A basic drug's solubility decreases as it proceeds distally towards the large intestine (pH 8.0) while it is soluble in the stomach and the upper or proximal region of the small intestine. Thus, a poorly soluble basic drug will lead to less drug being available for absorption in the lower or distal intestine. The inclusion of the organic acid within the formulation has overcome this problem. While not intending to be bound by any particular theory, it is believed that the formulation with the organic acid creates a microenvironment of low pH to enhance the solubility of the drug within the dosage form as it moves down the GI tract.

Accordingly, the present invention includes a controlled release solid pharmaceutical composition adapted for oral administration comprising:

a therapeutically effective amount of at least one basic drug having a water solubility of less than 1 part per 30 parts water;

a water-soluble alginate salt;

a complex salt of alginic acid, and an effective amount of an organic carboxylic acid to facilitate dissolution of the basic drug.

A particular aspect of the present invention is the preparation of a once daily dosage regimen for clarithromycin which currently is administered twice daily as a 250 mg or 500 mg tablet depending on the type of bacterial infection to be treated. The exact site of clarithromycin absorption in vivo is uncertain. However, it is known that clarithromycin is very soluble in the stomach (pH 1.2) and fairly soluble in the upper region of the small intestine (pH 5.0) where absorption is most likely to occur. Because the drug's solubility decreases in the lower intestine (pH 6 to 8), this leads to less drug being available for absorption. The present invention provides a way of overcoming this problem by using the alginate formulation with an organic acid, particularly, for example, citric acid.

Accordingly, a second aspect of the present invention is a controlled release, solid pharmaceutical composition adapted for oral administration of a once a day dosage regimen comprising:

about 500 mg of clarithromycin;

from about 75 to 400 mg of sodium alginate;

from about 10 to 400 mg of sodium-calcium alginate, and about 128 mg of citric acid.

DETAILED DESCRIPTION OF THE PREFERRED EMBODIMENT

The object of the present invention is to provide a controlled release pharmaceutical composition where a poorly soluble basic drug may be released continually from the dosage form as it proceeds through the GI tract.

The present invention thus provides for a once a day daily dose regimen for at least one poorly soluble basic drug by administering a controlled release, solid pharmaceutical composition adapted for oral administration to a patient in need thereof. A preferred composition is in tablet form.

A poorly soluble or sparingly water-soluble basic drug is a drug that has a solubility of less than 1 part in 30 parts of water. The present invention may apply also to even less soluble drugs for example up to a solubility of one part in 10,000 parts water.

By way of example, sparingly soluble basic drugs may include antibiotics such as, for example, sulfamethoxazole with a solubility of 1 in 3,400 (parts of water); tetracycline, 1 in 2,500; metronidazole and cimetidine (a histamine $H_2$ receptor antagonist for treating ulcers), both about 1 in 100 to 1 in 1,000; indapamide (an antihypertense/diuretic), 1 in more than 10,000; atenolol (an antihypertensive), about 1 in 30 to 1 in 100; diazepam (tranquilizer), ranging from 1 in 1,000 to 1 in 10,000.

As a preferred basic drug, the present invention includes macrolides which are also poorly soluble. Examples of macrolides are erythromycin with a solubility of one part in 1,000 parts of water; dirithromycin, with similar solubility properties as erythromycin; josamycin, midecamycin, kitasamycin, all three being very slightly soluble in water, ranging from about 1 in 1,000 to 1 in 10,000; and tylosin which is used for veterinary purposes only and with a solubility ranging from about 1 in 100 to 1 in 1,000. Other macrolides which may be included are, for example, roxithromycin, rokitamycin, oleandomycin, miocamycin, flurithromycin, rosaramicin, azithromycin, and compounds designated ABT-229 or ABT-269. The most preferred macrolide for the present invention is clarithromycin having a solubility of about one part in 1,000 parts of water.

The pharmaceutical composition of the present invention may include other drugs in combination with a poorly soluble basic drug wherever known combination therapy is required or beneficial.

Thus, for example, with macrolides, erythromycin or clarithromycin may be formulated in combination with a preparation for standard therapy of gastritis, ulcers or gastroesophagal reflux disease (GERD), such as preparations containing anti-ulcer or anti-gastritis medicaments; e.g., selected among gastric secretion inhibiting compounds such as omeprazole, cimetidine, ranitidine, lansoprazole, pantoprazole, sucralfate, famotidine, or nizatidine, or antacids such as magnesium hydroxide, aluminum hydroxide, sodium carbonate, sodium hydrogen carbonate, simethicone or aluminum magnesium hydroxide or hydrate thereof (such as the monohydrate known as magaldrate).

Another macrolide, particularly erythromycin or clarithromycin, pharmaceutical composition of the present invention may be adapted to be administered in combination with a preparation containing bismuth salts such as bismuth subcitrate, bismuth subsalicylate, bismuth subcarbonate, bismuth subnitrate or bismuth subgallate.

The amount of drug or drugs in the pharmaceutical composition may vary from about 40 to 75% of the total composition or tablet. For clarithromycin, the amount may preferably vary over 50% and up to 75% of the weight of the total composition or tablet.

The release rate of the formulation is controlled using a matrix based on a water-soluble alginate salt and a complex salt of alginic acid.

While sodium alginate is normally employed in the practice of this invention, the sodium cation may be replaced by another cation; e.g., potassium or other alkaline metal, magnesium, or ammonium to yield a soluble alginate salt. Thus, the alginate could also be, for example, potassium alginate or ammonium alginate.

The complex salt of alginic acid is a sodium-calcium complex salt of alginic in which the amount of calcium is precisely controlled, and which is self-gelling without the necessity of reacting with the stomach acid or additional calcium ions. While sodium-calcium alginate is normally employed in the practice of this invention, the sodium cation may be replaced by another cation that yields a soluble alginate salt; e.g., potassium or other alkaline metal, magnesium, or ammonium, and the calcium cation can also be replaced by another polyvalent cation (except for magnesium) that yields an insoluble alginate salt; e.g., strontium, iron, or barium. The most preferable preparations described herein typically include sodium alginate, for example, that manufactured and sold by Alginate Industries, Ltd., England, under the trademark "Manucol", and sodium-calcium alginate manufactured and sold by Kelco Division of Merck and Co., Inc., San Diego, Calif., U.S.A., under the trademark "Kelset".

The weight ratio of soluble alginate salt to complex salt of alginic acid may vary from about 16:1 to 1:1, preferably from about 8:1 to 2:1. The same ratio of course applies to the ratio of sodium alginate to sodium-calcium alginate. The combination of soluble alginate and complex salt to form an insoluble salt has been described in the art from European Patent 188040, as mentioned above, to provide controlled release formulations.

The organic acid required in the control release formulation of the present invention is an amount of acid effective to create a micro-environment of low pH, less than 7.0, in the vicinity of the hydrating dosage form. Viewed differently, an effective amount of organic acid is the amount which facilitates dissolution of the basic drug throughout the GI tract. The precise amount may vary depending on the acid used and the choice of basic drug as will be known to one skilled in the art. The ratio is a molar ratio and may vary from about 0.2:1 to 5:1 of acid to drug. Preferably, a molar ratio of 1:1 of acid to drug is used.

The organic acid for purposes of the present invention includes any organic carboxylic acid, preferably an aliphatic organic carboxylic acid having anywhere from $C_3$–$C_{20}$ carbon atoms. Preferred are, for example, tartaric acid, malic acid, succinic acid, glutaric acid, glutamic acid, maleic acid, mandelic acid and citric acid. The most preferred acid is citric acid.

A particular and preferred embodiment of the present invention is a controlled release, solid pharmaceutical composition adapted for oral administration of a once a day dosage regimen comprising:

about 500 mg of clarithromycin;
from about 75 to 400 mg of sodium alginate;
from about 10 to 400 mg of sodium-calcium alginate, and about 128 mg of citric acid.

Preferably, the composition contains from about 80 to 200 mg of sodium alginate and from about 10 to 40 mg of sodium-calcium alginate. Most preferably, the composition contains about 120 mg of sodium malginate and about 15 mg of sodium calcium alginate.

The composition is also preferably in the form of a tablet but may also be in capsule or pellet/granule form.

Other ingredients usually used in a preparation in accordance with the invention may include pharmaceutically acceptable excipients, such as preservatives, diluents; e.g., starch or microcrystalline cellulose; binders such as starch, polyvinyl pyrrolidone (povidone) and sodium carboxymethylcellulose; glidants or lubricants, such as talc and magnesium stearate; bulking agents such as lactose; and approved coloring agents. The dosage form may also be coated with materials not specifically designed for control or modification of drug release.

The preparation may be processed into tablets, suppositories or used for filling capsules. The preparation may also be coated when desired, for example, to mask an otherwise bitterly tasting preparation.

By way of example of the present invention, bioavailability studies on a representative formulation of the present invention containing clarithromycin, 500 mg, was found to meet the acceptance criteria for a successful once daily dosage formulation. This means that it achieved an area under the curve $AUC_{0-24}$ at least equivalent to the 250 mg twice a day (BID) dose regimen, and clarithromycin plasma concentrations at 24 hours were similar to the 250 mg BID dose regimen.

EXAMPLES

Example 1

Tablet Manufacturing Details

1a. Granulation of controlled release

All tablet formulations used the following general manufacturing method. The active drug, polymer, binding agent and remaining excipients were screened through a 850 μm aperture screen to remove any large agglomerates. The screened material was then dry blended using a planetary mixer set at the lowest speed for 5 minutes. The blended material was granulated by adding a 50/50 v/v solution of alcohol and water in small amounts until a suitable granulated mass was obtained. The wet mass was passed through a 4.0 mm aperture screen on to paper lined trays and dried in a hot air oven at 50° C. until the granule had a moisture content of less than 4% w/w (determined using Sartorious IR balance. Model: YTC01L. Conditions: 98° C. for 15 minutes). Finally, the dried granule was passed through a 850 μm aperture screen and blended with tablet lubricants for 5 minutes, using a planetary mixer set at the lowest speed.

1b. Compression

Tablets were compressed using a rotary tablet machine, fitted with ovaloid punches. Individual formulations A, B, and C were compressed to a tablet crushing strength which produced tablets of suitable thickness and friability. The tablet compositions are given in Table 1.

TABLE 1

| | Formulation: | | |
|---|---|---|---|
| Ingredients | A mg/tablet | B mg/tablet | C mg/tablet |
| Clarithromycin | 500 | 500 | 500 |
| Citric Acid Anhydrous USP | 128 | 128 | 128 |
| Sodium alginate | 80 | 120 | 180 |
| Sodium calcium alginate | 10 | 15 | 22.5 |
| Lactose 300 mesh | 100 | 100 | 100 |
| Povidone K (29-32) | 30 | 30 | 30 |

TABLE 1-continued

| | Formulation: | | |
|---|---|---|---|
| Ingredients | A mg/tablet | B mg/tablet | C mg/tablet |
| Talc, purified, powder | 30 | 30 | 30 |
| Stearic acid | 21 | 21 | 21 |
| Magnesium stearate | 10 | 10 | 10 |

Example 2

Bioavailability Study

2a. Materials and Supplies

A study compared the plasma concentration profiles of the three 500 mg once-daily (QD) formulations A, B, and C, above, with a twice daily dosing regimen of the comercially available 250 mg BIAXIN® tablet as a control (i.e. 250 mg BID, herein referred to Formulation D) at steady state. The acceptance criteria for a successful QD formulation were:

- $AUC_{0-24}$ at least equivalent to the 250 mg twice a day (BID) dosing regimen.
- Clarithromycin plasma concentrations at 24 hours equivalent to the 250 mg BID dosing regimen.

2b. Study Design and Results

The study was conducted as a Phase I, multi dose, open, randomised, four-period, balanced crossover study. Suitable patients were screened with a complete history, physical examination and laboratory profile, including assessment of hematological, renal, and liver parameters.

Eight healthy male volunteers between 18–50 years of age were dosed on the morning of days 1, 2 and 3 in each of the four study periods. Formulation D (BIAXIN® clarithromycin 250 mg) was also dosed on the evening on days 1, 2, and 3 in each of the study periods. Each subject received all formulations upon study completion.

Blood samples were collected prior to dosing on day 3 (0 hour) and at 1, 2, 3, 4, 6, 8, 10, 12, 16, and 24 hours after dosing. All samples were transferred to heparinised collection tubes and centrifuged. The separated plasma was split into equal volumes and transferred into appropriately labelled tubes and frozen immediately. The plasma samples were kept frozen until assayed.

Plasma samples were assayed using the large plate bioassay. This method measured total antibiotic activity, and expresses the results in terms of clarithromycin, mcg/ml.

2c. Data and Statistical Analysis

The bioequivalence of the three once daily formulations with the standard tablet was assessed by a two, one-sided t-test procedure. The 90% confidence intervals were calculated from analysis of the natural logarithms of AUC, $C_{max}$ and concentration at 24 hours. These were obtained by exponetiating the endpoints of the 90% confidence intervals for the difference in mean logarithms. Bioequivalence between formulations is inferred if these limits lay within the range of 0.80 to 1.25. In addition, 90% confidence intervals for the ratios of means were obtained from analysis of untransformed AUC and concentration at 24 hours. The results of this analysis are summarized in Tables 3, 4, and 5. The pharmacokinetic data are shown in Table 2.

TABLE 2

Pharmacokinetic Data

| Parameter | Formula D (250 mg BID) | Formula A | Formula B | Formula C |
|---|---|---|---|---|
| $AUC_{0-24}$ mcg.h/ml (range) | 32.16* (25.66–42.70) | 31.44 (21.16–38.50) | 32.32 (24.65–40.78) | 28.69 (24.61–32.74) |
| $C_{max}$ mcg/ml (range) | 2.28 (1.49–3.34) | 2.42 (1.53–3.26) | 2.41 (1.81–3.07) | 2.00 (1.62–2.40) |
| $T_{max}$ Hours (range) | 2 (1–4) | 6 (3–8) | 6 (3–8) | 6 (4–10) |
| Concentration mcg/ml at 24 hr (range) | 0.72 (0.53–1.05) | 0.57 (0.33–0.91) | 0.65 (0.30–0.87) | 0.66 (0.37–0.91) |

*As the plasma sampling program did not fully monitor the second standard tablet, $AUC_{0-24}$ value was calculated by multiplying the $AUC_{0-12}$ value by 2.

TABLE 3

Results of Statistical Analysis AUC

| | | Relative Bioavailability (90% confidence intervals) | |
|---|---|---|---|
| Formula | $AUC_{0-24}$ mcg.h/ml | Untransformed data | Ln transformed data |
| A | 31.44 | 0.98 (0.86–4.10) | 0.98 (0.84–1.14) |
| B | 32.32 | 1.01 (0.88–1.14) | 1.01 (0.88–1.16) |
| C | 28.69 | 0.89 (0.80–0.98) | 0.90 (0.80–1.02) |

TABLE 4

Results of Statistical Analysis Cmax

| | | Relative Bioavailability (90% confidence intervals) | |
|---|---|---|---|
| Formula | $C_{max}$ mcg/ml | Untransformed data | Ln transformed data |
| A | 2.42 | 1.06 (0.86–1.26) | 1.07 (0.87–1.32) |
| B | 2.41 | 1.06 (0.86–1.26) | 1.08 (0.90–1.31) |
| C | 2.00 | 0.88 (0.75–1.01) | 0.90 (0.76–1.06) |

TABLE 5

Results of Statistical Analysis Concentration at 24 Hours

| | | Relative Bioavailability (90% confidence intervals) | |
|---|---|---|---|
| Formula | $C_{max}$ mcg/ml | Untransformed data | Ln transformed data |
| A | 0.57 | 0.79 (0.62–0.99) | 0.79 (0.63–0.99) |
| B | 0.65 | 0.90 (0.79–1.01) | 0.89 (0.68–1.15) |
| C | 0.66 | 0.92 (0.76–1.08) | 0.90 (0.71–1.15) |

2d. Discussion

The mean AUC ratio, at 90% confidence limits, show that Formulations A, B and C are bioequivalent with the standard dosing regimen. All three formulations showed therapeutic levels at $C_{24}$ hours. Cmax limits (untransformed) are acceptable for most formulations. All three once daily formulations demonstrate extended absorption of clarithromycin when compared with the standard formulation.

Formulations A and B, despite containing different quantities of alginates, produced similar in vivo profiles. However, previous studies have shown that reproducibility of release profiles is improved by increasing the quantity of alginate. Therefore formulation B showed best overall results.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A controlled release, solid pharmaceutical composition adapted for oral administration comprising:

a therapeutically effective amount of at least one basic drug having a water solubility of less than 1 part per 30 parts water;

a water-soluble alginate salt;

a complex salt of alginic acid, wherein the cation yielding an insoluble salt is selected from the group consisting of calcium, strontium, iron, and barium;

and an organic carboxylic acid to facilitate dissolution of the basic drug, wherein the weight ratio of the water-soluble salt to the complex salt of alginic acid varies from 16:1 to 1:1, and the molar ratio of the carboxylic acid to the drug varies from 0.2:1 to 5:1.

2. The composition of claim 1, in tablet form.

3. The composition of claim 1, in the form of a once a day dosage regimen.

4. The composition of claim 1, wherein the basic drug is a macrolide.

5. The composition of claim 4, wherein the macrolide is clarithromycin.

6. The composition of claim 1, wherein the water-soluble alginate salt is sodium alginate.

7. The composition of claim 1, wherein the complex salt of alginic acid is sodium-calcium alginate.

8. The composition of claim 1, wherein the organic carboxylic acid is selected from the group consisting of tartaric, malic, succinic, glutaric, glutamic, maleic, mandelic and citric acid.

9. The composition of claim 8, wherein the organic carboxylic acid is citric acid.

10. The composition of claim 1, wherein the weight ratio of sodium alginate to sodium-calcium alginate is about 16:1 to 1:1.

11. The composition of claim 1, wherein the weight ratio of sodium alginate to sodium-calcium alginate is about 8:1 to 2:1.

12. The composition of claim 1, wherein the molar ratio of organic acid to basic drug is about 1:1.

13. The composition of claim 1, wherein the basic drug is selected from the group consisting of sulfamethoxazole, metronidazole, cimetidine, indapamide, atenolol and diazepam.

14. The composition of claim 4, wherein the macrolide is selected from the group consisting of erythromycin, dirithromycin, azithromycin, roxithromycin and ABT-229.

15. A controlled release, solid pharmaceutical composition adapted for oral administration of a once a day dosage regimen comprising:

about 500 mg of clarithromycin;

from about 75 to 400 mg of sodium alginate; from about 10 to 400 mg of sodium-calcium alginate, and about 128 mg of citric acid.

16. The composition of claim 14 comprising:

from about 80 to 200 mg of sodium alginate, and from about 10 to 40 mg of sodium-calcium alginate.

17. The composition of claim 15 comprising:

about 120 mg of sodium alginate, and about 15 mg of sodium-calcium alginate.

* * * * *